(12) United States Patent
Imamura et al.

(10) Patent No.: US 12,709,731 B2
(45) **Date of Patent: *Aug. 18, 2026**

(54) METHOD OF PRODUCING BIOLOGICAL MATERIAL

(71) Applicant: NTT, Inc., Tokyo (JP)

(72) Inventors: Sosuke Imamura, Musashino (JP); Kazuhiro Takaya, Musashino (JP)

(73) Assignee: NTT, Inc., Tokyo (JP)

(*) Notice: Subject to any disclaimer, the term of this patent is extended or adjusted under 35 U.S.C. 154(b) by 298 days.

This patent is subject to a terminal disclaimer.

(21) Appl. No.: 18/563,922

(22) PCT Filed: Jun. 15, 2021

(86) PCT No.: PCT/JP2021/022699

§ 371 (c)(1), (2) Date: Nov. 24, 2023

(87) PCT Pub. No.: WO2022/264267

PCT Pub. Date: Dec. 22, 2022

(65) Prior Publication Data

US 2024/0279593 A1 Aug. 22, 2024

(51) Int. Cl.

*C12N 1/12* (2026.01)
*C12P 7/64* (2022.01)
*C12P 19/04* (2006.01)

(52) U.S. Cl.

CPC .................. *C12N 1/12* (2013.01); *C12P 7/64* (2013.01); *C12P 19/04* (2013.01); *C12N 2500/30* (2013.01); *C12N 2529/10* (2013.01)

(58) Field of Classification Search

None

See application file for complete search history.

(56) References Cited

PUBLICATIONS

Marino et al (Autophagy 10:5,930-932, 2014).*
Frostl et al (Arch. Microbiol, 169:129-135, 1998).*
Amano et al (Fisheries Sci., 60:449-454, 1994).*
Kirst et al., "Truncated Photosystem Chlorophyll Antenna Size in the Green Microalga *Chlamydomonas reinhardtii* Upon Deletion of the TLA3-CpSRP43 Gene", Plant Physiology, downloaded on May 9, 2021, vol. 160, No. 4, pp. 2251-2260.
Notification of Transmittal of Translation of the International Preliminary Report on Patentability mailed Dec. 28, 2023 in International Patent Application No. PCT/JP2021/022699, 6 pages. (Submitting English translation only.).

* cited by examiner

*Primary Examiner* — Brian Gangle
(74) *Attorney, Agent, or Firm* — XSENSUS LLP

(57) ABSTRACT

A technique capable of achieving production of a biological material using photosynthetic microorganisms at low cost is provided. A method of producing a biological material includes culturing photosynthetic microorganisms in a culture medium containing dimethyl 2-oxoglutarate while the photosynthetic microorganisms are irradiated with light to cause the photosynthetic microorganisms to proliferate, and then collecting a substance produced by or accumulated in the photosynthetic microorganisms.

10 Claims, 5 Drawing Sheets

METHOD OF PRODUCING BIOLOGICAL MATERIAL

CROSS-REFERENCE TO RELATED APPLICATION

The present application is based on PCT filing PCT/JP2021/022699, filed Jun. 15, 2021, the entire contents of which are incorporated herein by reference.

TECHNICAL FIELD

The present invention relates to a method of producing a biological material.

BACKGROUND ART

Oils and fats produced by algae can be utilized as a raw material for biofuels, for example. Carbohydrates produced by algae can be utilized as a raw material for, for example, fuel additives, pharmaceuticals, cosmetics, and plastic products.

In the case where oils and fats and starch are produced using microalgae on a large scale, an open pond may be used for culturing algae. As algae proliferate, the density of the algae cells in a microorganism-containing liquid containing the algae and the liquid culture medium becomes higher. When such circumstances occur in, for example, an open pond, most incident light is absorbed by algal cells near the liquid surface.

When irradiated with light having an intensity exceeding a light saturation point, the algal cells dissipate as heat the surplus portion of the absorbed photon energy that is not utilized in photosynthesis, to protect their own photosynthesis function. If the intensity of the light radiated to the algae cells exceeds the light saturation point near the liquid surface, a surplus portion of the energy absorbed by the algae cells near the liquid surface is dissipated as heat, and is not utilized for photosynthesis of the algae cells in the deep region.

In addition, in a situation where most incident light is absorbed by the algal cells near the liquid surface, light with a sufficient intensity does not reach the algal cells in the deep region. That is, when the algae proliferate and the intensity of light reaching the algae cells in the deep region becomes lower, the photosynthesis rate of the algae cells in the deep region decreases.

Accordingly, as the algae proliferate, the proliferation rate of the algae becomes lower.

Non-Patent Literature 1 describes a transformant of *Chlamydomonas reinhardtti* which has a smaller amount of chlorophyll per cell and a higher ratio a/b of chlorophyll a to chlorophyll b, as compared to a wild type thereof. Chlorophyll b serves as an antenna for collecting light, that is, light-harvesting pigments. On the other hand, chlorophyll plays a role as a reaction center directly involved in the electron transfer reaction of photosynthesis and a role as a light-harvesting pigment.

The transformant has a small amount of chlorophyll per cell. For this reason, the decrease in intensity of light reaching cells in the deep region caused by proliferation of the transformant is small. In addition, since the above-mentioned transformant has a high ratio a/b, the above-mentioned energy surplus is small in the cultivation thereof.

CITATION LIST

Non-Patent Literature

Non-Patent Literature 1: Truncated Photosystem Chlorophyll Antenna Size in the Green Microalga *Chlamydomonas reinhardtii* upon Deletion of the TLA3-CpSRP43 Gene. Henning Kirst, Jose Gines Garcia-Cerdan, Andreas Zurbriggen, Thilo Ruehle, Anastasios Melis. Plant Physiology. (2012) 160:2251-2260.

SUMMARY OF INVENTION

An object of the present invention is to provide a technique that makes it possible to easily mitigate a decrease in a proliferation rate of photosynthetic microorganisms due to an increase in a cell density.

According to a first aspect of the present invention, there is provided a method of producing a biological material, including culturing a photosynthetic microorganism in a culture medium containing dimethyl 2-oxoglutarate while the photosynthetic microorganism is irradiated with light to cause the photosynthetic microorganism to proliferate, and then collecting a substance produced by or accumulated in the photosynthetic microorganism.

According to a second aspect of the present invention, there is provided a method of producing a biological material, including culturing a photosynthetic microorganism while the photosynthetic microorganism is irradiated with light in a culture medium to cause the photosynthetic microorganism to proliferate, then adding dimethyl 2-oxoglutarate to the culture medium, further culturing the photosynthetic microorganism in the culture medium containing dimethyl 2-oxoglutarate while the photosynthetic microorganism is irradiated with light to cause the photosynthetic microorganism to further proliferate, and then collecting a substance produced by or accumulated is the photosynthetic microorganism.

According to a third aspect of the present invention, there is provided a regulator for use in reducing an amount of light-harvesting pigments in a photosynthetic microorganism, containing dimethyl 2-oxoglutarate.

According to the present invention, a technique that makes it possible to easily mitigate a decrease in a proliferation rate of photosynthetic microorganisms due to an increase in a cell density is provided.

BRIEF DESCRIPTION OF DRAWINGS

FIG. 4 is a graph showing an example of the effect of addition of a regulator on the amount of chlorophyll a.

DESCRIPTION OF EMBODIMENTS

Figure 1:
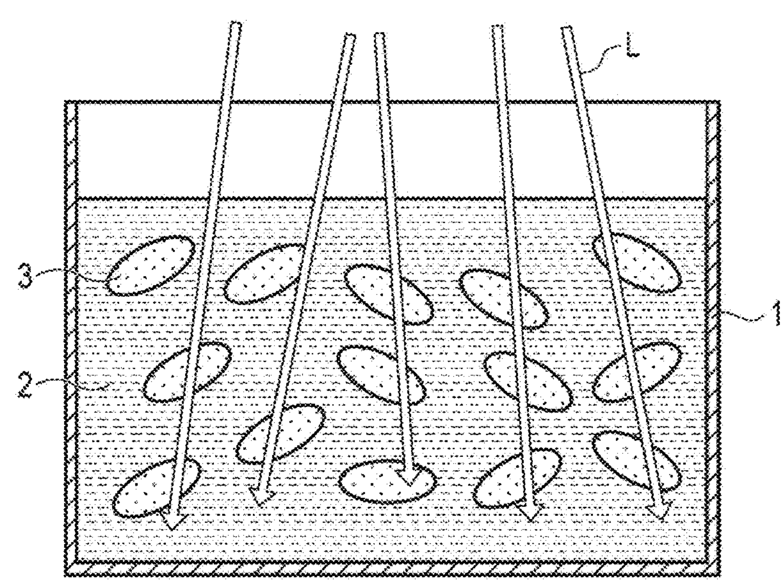
FIG. 1 is a diagram schematically illustrating a method of producing a biological material according to an embodiment of the present invention.

Hereinafter, embodiments of the present invention will be described. The embodiments described below are more specific implementations of any of the above-mentioned aspects. The items described below can be incorporated into each of the above-mentioned aspects alone or in combination.

In a method of producing a biological material according to an embodiment of the present invention, first, photosynthetic microorganisms are cultured in a culture medium. In this culture, the photosynthetic microorganisms are irradiated with light, for example, in the presence of carbon dioxide. For example, the photosynthetic microorganisms are irradiated with sunlight under the air atmosphere. This causes photosynthesis in the photosynthetic microorganisms and causes the photosynthetic microorganisms to proliferate.

The photosynthetic microorganisms are, for example, microorganisms that carry out oxygenic photosynthesis. The photosynthetic microorganisms are, for example, algae such as eukaryotic algae. The algae are preferably microalgae. Here, "microalgae" are, for example, photosynthetic eukaryotes, and is a unicellular organism or a colony thereof. The microalgae are, for example, unicellular green algae such as *Chlamydomonas reinhardtti* and *Botryococcus*, unicellular red algae such as *Cyanidioschyzon merolae*, or colonies thereof. The photosynthetic microorganisms may not be eukaryotes. The photosynthetic microorganisms may be prokaryotic organisms, for example, bacteria such as cyanobacteria. The prokaryotic organisms may be archaea.

As the culture medium, a culture medium containing all nutrients necessary for the proliferation and photosynthesis of photosynthetic microorganisms in a sufficient concentration is used. The culture medium is a liquid culture medium in this case. In addition, the above-mentioned cultivation is, for example, suspended cultivation. The suspended cultivation can be carried out, for example, in an open culture tank that is called an open pond. The suspended cultivation may be carried out in a closed system that is called a closed photobioreactor.

When the photosynthetic microorganisms proliferate, the density of cells in the microorganism-containing liquid containing the photosynthetic microorganisms and the culture medium increases. Accordingly, the intensity of light reaching the cells in the deep region away from the incident surface of light is reduced, and the photosynthesis rate of the cells in the deep region is reduced. As a result, the proliferation rate of the photosynthetic microorganisms is lowered.

Then, at any time point at which the proliferation rate of the photosynthetic microorganisms becomes lower, a regulator containing dimethyl 2-oxoglutarate represented by the following chemical formula (1) is added to the culture medium.

[C1]

Chemical Formula (1)

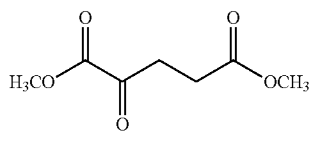

The regulator contains dimethyl 2-oxoglutarate. Dimethyl 2-oxoglutarate reduces the amount of light-harvesting pigments in the photosynthetic microorganisms as will be described below.

2-Oxoglutaric acid represented by the following chemical formula (2) is considered as one of signal substances for nitrogen deficiency in microorganisms. In photosynthetic microorganisms, generally, the light-harvesting pigments are decomposed and reduced under conditions in which nitrogen is deficient. Therefore, it is considered that addition of 2-oxoglutaric acid to the above-mentioned culture medium can cause a pseudo nitrogen-deficient state in the photosynthetic microbial cells, thereby inducing depigmentation.

[C2]

Chemical Formula (2)

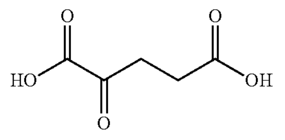

However, even if 2-oxoglutaric acid is added to the above-mentioned culture medium, depigmentation in the photosynthetic microbial cells is not induced and the proliferation rate does not become higher, either. This is because 2-oxoglutaric acid is not incorporated into the photosynthetic microbial cells.

Unlike 2-oxoglutaric acid, dimethyl 2-oxoglutarate is permeable to cell membranes. In addition, dimethyl 2-oxoglutarate exhibits the similar effect to that of 2-oxoglutaric acid in photosynthetic microbial cells. For this reason, when a regulator containing dimethyl 2-oxoglutarate is added to the above-mentioned culture medium, the amount of light-harvesting pigment in the photosynthetic microorganisms can be reduced.

The regulator may further contain a solvent. As the solvent, for example, a liquid having the same or almost the same composition as that of the culture medium used for culturing photosynthetic microorganisms can be used. When dimethyl 2-oxoglutarate is diluted in the solvent, the dimethyl 2-oxoglutarate can be easily supplied uniformly to the liquid surface of the microorganism-containing liquid, for example.

The timing at which the regulator is added is determined based on any of, for example, a light transmittance and turbidity of the microorganism-containing liquid, the number of cells per volume, the specific proliferation rate of photosynthetic microorganisms, and a rate of change thereof. According to one example, the timing at which a regulator is added is determined by comparing any one of the light transmittance and turbidity of the microorganism-containing liquid, the number of cells per volume, the specific proliferation rate of the photosynthetic microorganisms, and the change rate thereof with a predetermined threshold.

The regulator is preferably added so that a concentration of dimethyl 2-oxoglutarate of the mixed liquid containing the culture medium, the photosynthetic microorganisms, and the regulator is 5 mmol/L or higher, and more preferably added so that a concentration thereof is 20 mmol/L or higher. When the concentration decreases, the effect of reducing the amount of light-harvesting pigments in the photosynthetic microorganisms is reduced. A concentration thereof is preferably 100 mmol/L or lower. If a concentration thereof is increased, costs become higher, and proliferation of photosynthetic microorganisms is likely to be delayed as will be described later.

The regulator is supplied to the culture medium so that the concentration of dimethyl 2-oxoglutarate is substantially uniform in the entire culture medium, for example. The regulator may be supplied so that the concentration of dimethyl 2-oxoglutarate is higher in the vicinity of the surface (light incident surface) of the microorganism-containing liquid containing the culture medium and the photosynthetic microorganisms than in the deep region of the microorganism-containing liquid. Dimethyl 2-oxoglutarate may reduce the amount of light-harvesting pigments in the photosynthetic microorganisms while delaying proliferation of the photosynthetic microorganisms. For example, in the case where suspension culture of photosynthetic microorganisms in an open culture tank is performed, if the concentration of dimethyl 2-oxoglutarate near the liquid surface is made higher than that in the deep region, the amount of light-harvesting pigments contained in the photosynthetic microorganisms near the liquid surface can be reduced while a delay in propagation by dimethyl 2-oxoglutarate in the deep region is prevented. The above-mentioned concentration gradient can be realized, for example, by spraying the regulator on the liquid surface.

After the addition of the regulator to the culture medium, the cultivation similar to the above is continued to cause the photosynthetic microorganisms to further proliferate. The addition of the regulator to the culture medium reduces the amount of light-harvesting pigments contained in the photosynthetic microorganism near the liquid surface, for example. As a result, the light reaches the photosynthetic microbial cells in the deep region with a sufficient intensity, and the proliferation rate increases.

A time period required for the amount of light-harvesting pigments contained in the photosynthetic microorganisms is sufficiently reduced after the addition of the regulator differs according to the kind of the photosynthetic microorganisms. Generally, that time period is in the range of 3 hours to 48 hours. Thus, in order to further proliferate the photosynthetic microorganisms after the addition of the regulator, the culture period after the addition of the regulator is preferably 3 hours or more, and more preferably 12 hours or more. Although the culture period has no upper limit, it is preferable to set the culture period to 14 days or less in consideration of productivity.

Then, if necessary, the cycle in which the regulator is added to the culture medium and then photosynthetic microorganisms are cultured is repeated one or more times.

Thereafter, the substance produced by or accumulated in the photosynthetic microorganisms is collected. When the substance accumulated in the cells of the photosynthetic microorganism is collected, for example, hydrophobic substances are extracted from the photosynthetic microorganisms to obtain an extract containing the hydrophobic substances and the residue containing hydrophilic substances. Alternatively, hydrophilic substances are extracted from the photosynthetic microorganisms to obtain an extract containing hydrophilic substances and a residue containing the hydrophobic substances. When substances released to the outside of the cells out of the substances produced by the photosynthetic microorganisms are collected, the substances are collected from, for example, the culture medium. Here, as an example, a method for obtaining oils and fats or carbohydrates from photosynthetic microorganisms will be described.

For example, the photosynthetic microorganisms are first separated from the culture medium. In a case where suspended cultivation is carried out, at least a part of the culture medium is removed from the mixed liquid of the photosynthetic microorganisms and the culture medium, for example, by centrifugal separation or compression. Thereby, a concentrate containing photosynthetic microorganisms at a higher concentration than the previous mixed liquid is obtained. Then, the concentrate is dried to obtain a dried product composed of photosynthetic microorganisms.

Next, oils and fats are extracted from the dried product composed of photosynthetic microorganisms. An organic solvent is used as an extraction medium for extracting oils and fats. Thus, an extract containing the oils and fats is obtained and a residue containing carbohydrates is obtained.

In the case where oils and fats are produced, the extract is then purified if necessary. The purified product may be modified. In this way, oils and fats are obtained from the photosynthetic microorganisms. The oils and fats thus obtained can be used as a biofuel or a raw material thereof, for example.

In the case where carbohydrates are produced, for example, carbohydrates are extracted from the above residue. In a case where polysaccharides such as starch are extracted, for example, water is used as an extraction medium. Then, the extract is purified if necessary. The purified product may be modified. In this way, carbohydrates are obtained from the photosynthetic microorganisms. The carbohydrates can be utilized as a raw material for, for example, fuel additives, pharmaceuticals, cosmetics, and plastic products.

Various substances such as oils and fats, carbohydrates, hydrocarbons, amino acids, and the like are produced by and accumulated in photosynthetic microorganisms. The substances produced by and accumulated in the photosynthetic microorganisms are different according to the kind of photosynthetic microorganisms. Oils and fats are, for example, a neutral lipid such as triacylglycerol. Hydrocarbons are, for example, botryococcene. In addition, carbohydrates are, for example, starch or a combination of starch and one or more other carbohydrate components.

For example, oils and fats, carbohydrates, a purified product or a modified product thereof can be obtained by using the method. In addition, using a similar method thereto, other substances such as hydrocarbons and amino acids accumulated in the photosynthetic microorganisms, or a purified product or a modified product thereof can be obtained.

The substances produced by or accumulated in the photosynthetic microorganisms and acquired as described above, the substances obtained by performing post-treatment such as purification and modification to the above substances, or the substances obtained by using the above substances as raw materials are biological materials. The biological material may be a product, for example, a biofuel, a fuel additive, a pharmaceutical, a supplement, a physiologically active substance, a food, a cosmetic, or a plastic product. Alternatively, the biological material is one or more components or raw materials of the above-mentioned products.

In the method described above, a regulator is added to the culture medium. Thus, a decrease in the proliferation rate of the photosynthetic microorganisms caused by an increase in the cell density can be mitigated. This method will be described with reference to FIGS. 1 and 2.

Figure 2:
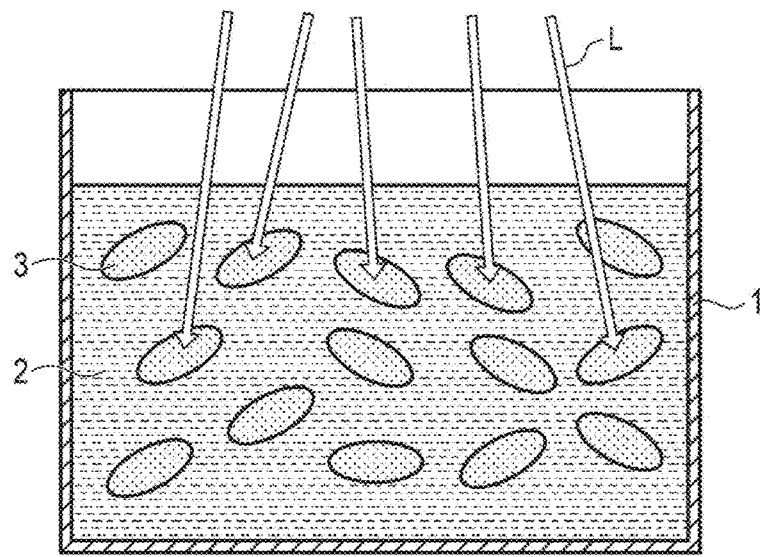
FIG. 2 is a diagram schematically illustrating a method of producing a biological material according to a comparative example.

FIG. 1 is a diagram schematically illustrating a method of producing a biological material according to an embodiment of the present invention. FIG. 2 is a diagram schematically illustrating a method of producing a biological material according to a comparative example. FIGS. 1 and 2 depict a state in which a microorganism-containing liquid containing a liquid culture medium 2 and the photosynthetic microorganisms 3 and accommodated in an open culture tank 1 is irradiated with sunlight L.

In a case where no regulator is added to the liquid culture medium 2 although the proliferation of the photosynthetic microorganisms 3 progresses and the density of the cells increases, most of sunlight L is absorbed by the photosynthetic microorganisms 3 near the liquid surface, and sunlight L with a sufficient intensity does not reach the photosynthetic microorganisms 3 in the deep region as illustrated in FIG. 2. Thus, the photosynthesis rate of the photosynthetic microorganisms 3 is low and the proliferation rate is low as well in the deep region.

On the other hand, in a case where a regulator is sprayed to the liquid culture medium 2, for example, after proliferation of the photosynthetic microorganisms 3 progresses and the density of the cells is increased, the amount of light-harvesting pigments contained in the photosynthetic microorganisms can be reduced at least near the liquid surface. Therefore, sunlight L with a sufficient intensity can reach the photosynthetic microorganisms 3 in the deep region as illustrated in FIG. 1.

As described above, there are known a transformant of *Chlamydomonas reinhardtti* having a smaller amount of chlorophyll per cell and a higher ratio a/b of chlorophyll a to chlorophyll b, as compared to a wild type thereof. This type of transformant has a small amount of chlorophyll per cell. For this reason, the decrease in intensity of light reaching cells in the deep region caused by proliferation of the transformant is small. In addition, since the transformant has a high ratio a/b, there is a little surplus energy to be dissipated as heat in this cultivation.

However, in order to obtain a transformant having properties similar to those of the above-mentioned transformant, a foreign gene is introduced into photosynthetic microorganism cells or a gene is modified through ultraviolet irradiation, and a strain having a desirable property among those obtained in this way, for example, a strain similar to that of the wild type except that having a smaller amount of the light-harvesting pigment per cell, needs to be isolated. Only a limited number of photosynthetic microorganisms are capable of gene transfer into their cells. In addition, particularly in a case where gene modification by ultraviolet irradiation is used, trial and error are required and a long time and a large amount of labor are required to obtain a transformant having desirable properties. Thus, reports on transformants of photosynthetic microorganisms having the above-mentioned properties are limited to several examples.

As described with reference to FIG. 1, in the above-described method, the amount of light-harvesting pigments contained in the photosynthetic microorganisms can be reduced at least near the liquid surface by adding a regulator to the culture medium. The addition of the regulator to the culture medium is much easier compared to acquisition of a genetic recombinant.

Thus, according to this method, a decrease in the proliferation rate of photosynthetic microorganisms caused by an increase in the cell density can be easily mitigated.

In addition, the above-mentioned transformant is a genetic recombinant. Therefore, even if a transformant having the above properties can be obtained, facilities for culturing such transformants are limited.

On the other hand, in the above-described method, the decrease in the proliferation rate of the photosynthetic microorganisms caused by the increase in the cell density can be mitigated without using genetic recombinants as the photosynthetic microorganisms. Therefore, it is not necessary to use a closed system to culture wild-type photosynthetic microorganisms. In addition, dimethyl 2-oxoglutarate is relatively inexpensive. Accordingly, the method can realize production of a biological material using photosynthetic microorganisms at low cost.

Furthermore, dimethyl 2-oxoglutarate is a derivative of 2-oxoglutaric acid which is a metabolite common to all organisms. Therefore, the above-described effects of the addition of the regulator containing dimethyl 2-oxoglutarate can be exhibited in all photosynthetic microorganisms.

[Tests]

The tests conducted by the inventors will be described below.

(Test 1)

Unicellular red algae were cultured in suspension under a light condition and a regulator was added thereto. An MA2 culture medium was used as a culture medium. *Cyanidioschyzon merolae* were used as unicellular red algae. Dimethyl 2-oxoglutarate was used as the regulator. Then, after the regulator was added, the culture was further continued for 18 hours.

The above-mentioned cultivation was carried out for each case where the final concentrations of dimethyl 2-oxoglutarate were adjusted to 10, 20, 40 and 80 mmmol/L (=mM). In addition, cultivation was also carried out in a similar manner except that the addition of dimethyl 2-oxoglutarate was omitted.

Thereafter, each of microorganism-containing liquids containing unicellular red algae and the culture medium was imaged.

In addition, cultivation was carried out in a similar manner except that 2-oxoglutaric acid was used instead of using dimethyl 2-oxoglutarate. Thereafter, each of dispersion microorganism-containing liquids containing unicellular red algae and the culture medium was imaged.

Figure 3:
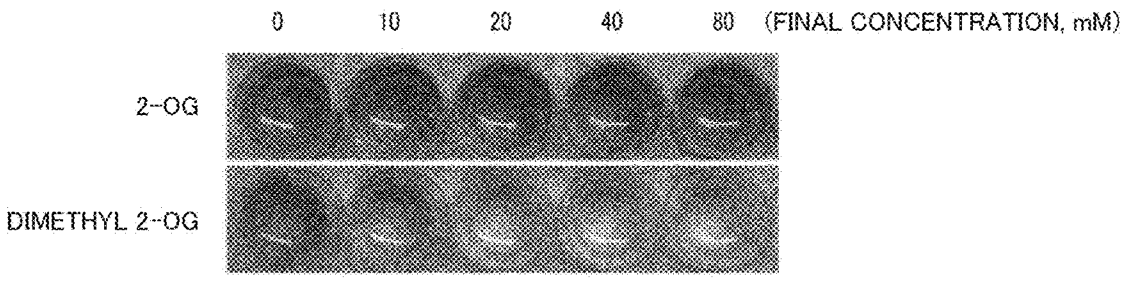
FIG. 3 shows an image obtained by imaging a microorganism-containing liquid after cultivation.

FIG. 3 is an image obtained by imaging the microorganism-containing liquids after cultivation. In FIG. 3, "2-OG" and "dimethyl 2-OG" represent 2-oxoglutaric acid and dimethyl 2-oxoglutarate, respectively.

As shown in FIG. 3, when 2-oxoglutaric acid was added to the culture medium, the microorganism-containing liquids have the same color as that in the case with no regulator added even if the final concentration was adjusted to be higher. That is, the addition of 2-oxoglutaric acid to the culture medium little contributed to a reduction of light-harvesting pigments.

On the other hand, when dimethyl 2-oxoglutarate was added to the culture medium, the colors of the microorganism-containing liquids were lighter than those of the microorganism-containing liquids with no regulator added even if the final concentration was adjusted to be low. Especially, when the final concentration of dimethyl 2-oxoglutarate was adjusted to 20 mmol/L or higher, the microorganism-containing liquid became substantially colorless. That is, the addition of dimethyl 2-oxoglutarate to the culture medium greatly contributes to a reduction of light-harvesting pigments.

(Test 2)

Unicellular red algae were cultured in suspension under a light condition and a regulator was added thereto. An MA2 culture medium was used as a culture medium. *Cyanidioschyzon merolae* were used as unicellular red algae. Dimethyl 2-oxoglutarate was used as the regulator. The regulator was added so that the final concentration of dimethyl 2-oxoglutarate was 2 mmol/L. After the regulator was added, the cultivation was further continued. Then, the amounts of chlorophyll a contained in the microorganism-containing liquids were determined immediately before the regulator was added, 6 hours after the regulator was added, and 24 hours after the regulator was added.

In addition, in parallel with the cultivation, cultivation was carried out as described above in a similar manner except that no regulator was added. The amount of chlorophyll a contained in the microorganism-containing liquid was also determined in the same manner as described above.

Figure 4:
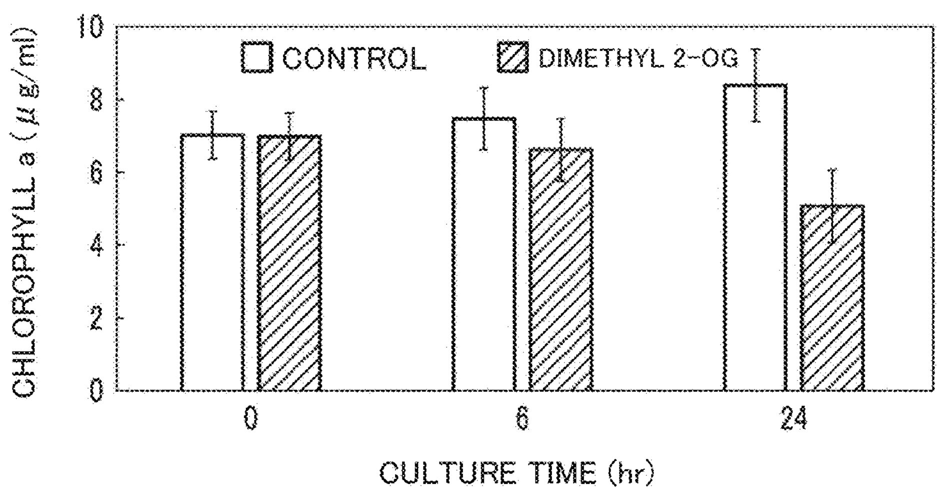

FIG. 4 is a graph showing an example of the effect of the addition of the regulator on the amounts of chlorophyll a. FIG. 4 shows the average value of the three independent test results, and the standard deviations are shown by error bars. In addition, in FIG. 4, "control" shows the results obtained for unicellular red algae cultured without adding a regulator to the culture medium. Furthermore, "dimethyl 2-OG" indicates the results obtained for unicellular red algae cultured by adding dimethyl 2-oxoglutarate to the culture medium as a regulator.

As shown in FIG. 4, the amount of chlorophyll a increased according to the culture time in the case of unicellular red algae cultured with no regulator added. On the other hand, the amount of chlorophyll a decreased according to the culture time in the case of unicellular red algae cultured by adding a regulator.

(Test 3)

Cultivation was carried out in a similar manner to that in the test 2 and the amounts of phycocyanin contained in the microorganism-containing liquids were determined in every culture time.

Figure 5:
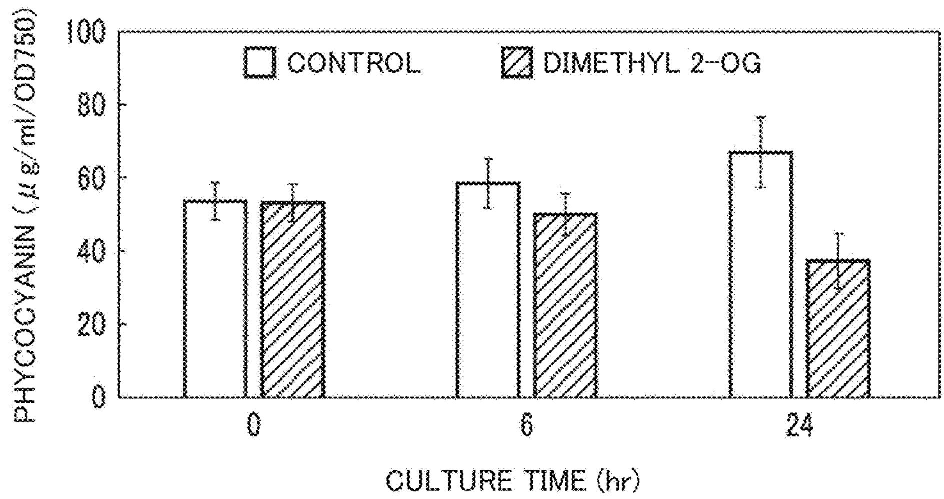
FIG. 5 is a graph showing an example of the effect of the addition of a regulator on the amount of phycocyanin.

FIG. 5 is a graph showing an example of the effect of the addition of a regulator on the amount of phycocyanin. FIG. 5 shows the average value of the three independent test results, and the standard deviations are shown by error bars. In addition, in FIG. 5, "control" shows the results obtained for unicellular red algae cultured without adding a regulator to the culture medium. Furthermore, "dimethyl 2-OG" indicates the results obtained for unicellular red algae cultured by adding dimethyl 2-oxoglutarate to the culture medium as a regulator.

As shown in FIG. 5, the amount of phycocyanin increased according to the culture time in the case of unicellular red algae cultured with no regulator added. On the other hand, the amount of phycocyanin decreased according to the culture time in the case of unicellular red algae cultured by adding a regulator.

REFERENCE SIGNS LIST

1 Open culture tank
2 Liquid culture medium
3 Photosynthetic microorganism
L Sunlight

The invention claimed is:

1. A method of producing a biological material, comprising:

culturing a photosynthetic microorganism in a culture medium containing dimethyl 2-oxoglutarate while the photosynthetic microorganism is irradiated with light to cause the photosynthetic microorganism to proliferate; and then collecting a substance produced by or accumulated in the photosynthetic microorganism.

2. The method of producing a biological material according to claim 1, wherein the photosynthetic microorganism is of a wild type.

3. The method of producing a biological material according to claim 1, wherein the photosynthetic microorganism is cultured in an open culture tank.

4. The method of producing a biological material according to claim 1, wherein a dimethyl 2-oxoglutarate concentration near a surface of a microorganism-containing liquid containing the culture medium and the photosynthetic microorganism is set to be higher than in a deep region of the microorganism-containing liquid.

5. The method of producing a biological material according to claim 1, wherein collecting the substance includes extracting one of a hydrophobic substance and a hydrophilic substance from the photosynthetic microorganism to obtain an extract and a residue.

6. A method of producing a biological material, comprising:

culturing a photosynthetic microorganism while the photosynthetic microorganism is irradiated with light in a culture medium to cause the photosynthetic microorganism to proliferate;

then adding dimethyl 2-oxoglutarate to the culture medium;

further culturing the photosynthetic microorganism in the culture medium containing dimethyl 2-oxoglutarate while the photosynthetic microorganism is irradiated with light to cause the photosynthetic microorganism to further proliferate; and then collecting a substance produced by or accumulated in the photosynthetic microorganism.

7. The method of producing a biological material according to claim 6, wherein the photosynthetic microorganism is of a wild type.

8. The method of producing a biological material according to claim 6, wherein the photosynthetic microorganism is cultured in an open culture tank.

9. The method of producing a biological material according to claim 6, wherein a dimethyl 2-oxoglutarate concentration near a surface of a microorganism-containing liquid containing the culture medium and the photosynthetic microorganism is set to be higher than in a deep region of the microorganism-containing liquid.

10. The method of producing a biological material according to claim 6, wherein collecting the substance includes extracting one of a hydrophobic substance and a hydrophilic substance from the photosynthetic microorganism to obtain an extract and a residue.

* * * * *